US00PP30108P3

(12) United States Plant Patent
Klemm et al.

(10) Patent No.: US PP30,108 P3
(45) Date of Patent: Jan. 15, 2019

(54) ***PELARGONIUM* PLANT NAMED 'KLEPZ16424'**

(50) Latin Name: *Pelargonium zonale*
Varietal Denomination: KLEPZ16424

(71) Applicant: Klemm+Sohn GmbH & Co. KG, Stuttgart (DE)

(72) Inventors: Nils Klemm, Stuttgart (DE); Martin Glawe, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 7 days.

(21) Appl. No.: 15/731,359

(22) Filed: Jun. 1, 2017

(65) Prior Publication Data

US 2017/0367237 P1 Dec. 21, 2017

(30) Foreign Application Priority Data

Jun. 16, 2016 (CH) ..... PBR 16-3070

(51) Int. Cl.
*A01H 5/02* (2018.01)
*A01H 6/42* (2018.01)

(52) U.S. Cl.
USPC ..... Plt./327
CPC ..... *A01H 6/42* (2018.05); *A01H 5/02* (2013.01)

(58) Field of Classification Search
USPC ..... Plt./263.1, 324, 325, 327
See application file for complete search history.

*Primary Examiner* — Susan McCormick Ewoldt
*Assistant Examiner* — Karen M Redden
(74) *Attorney, Agent, or Firm* — Bethany Reid Roahrig; Cochran Freund & Young LLC

(57) ABSTRACT

A new *pelargonium* plant particularly distinguished by large, salmon orange colored flowers with red-purple eyes and an upright growth habit, is disclosed.

1 Drawing Sheet

Genus and species: *Pelargonium zonale.*
Variety denomination: 'KLEPZ16424'.

CROSS REFERENCE TO RELATED APPLICATION

The present application claims priority to Switzerland Plant Variety Protection Application No. 16-3070, as filed on Jun. 16, 2016, the entire contents are herein incorporated by reference for all the application teaches and discloses.

BACKGROUND OF THE NEW PLANT

The present invention comprises a new and distinct variety of *pelargonium*, botanically known as *Pelargonium zonale* and hereinafter referred to by the variety name 'KLEPZ16424'. 'KLEPZ16424' originated from a cross-combination in September 2010 in Stuttgart, Germany between the female *pelargonium* variety 'KLEPZ05129', also known as SUNRISE Mandarin (U.S. Plant Pat. No. 18,621) and the proprietary male *pelargonium* variety SUNRISE Racing (unpatented).

Seeds from the cross-combination were obtained and sown and plants were grown for evaluation. A single plant was selected in June 2011 and subsequently named 'KLEPZ16424'. In August 2011 'KLEPZ16424' was first vegetatively propagated in Stuttgart, Germany by vegetative cuttings from branches. 'KLEPZ16424' was found to reproduce true to type in successive generations of asexual propagation via vegetative cuttings in Stuttgart, Germany.

SUMMARY

The following are the most outstanding and distinguishing characteristics of this new variety when grown under normal horticultural practices in Stuttgart, Germany.

1. Large salmon-orange colored flowers with re-purple eyes; and
2. An upright growth habit.

DESCRIPTION OF THE PHOTOGRAPH

This new *pelargonium* plant is illustrated by the accompanying photograph which shows an overall view of the plant. The photograph is of an approximately nine to ten-week-old plant grown in Stuttgart, Germany under greenhouse conditions in May 2015. The colors shown are as true as can be reasonably obtained by conventional photographic procedures.

DESCRIPTION OF THE NEW VARIETY

The following detailed descriptions set forth the distinctive characteristics of 'KLEPZ16424'. The data which define these characteristics were collected from asexual reproductions carried out in Stuttgart, Germany. Data was collected on plants grown three months after planting in Stuttgart, Germany under a glass covered greenhouse in April 2017. Color references are to The R.H.S. Colour Chart of The Royal Horticultural Society of London (R.H.S.), $5^{th}$ edition (2007).

Classification:

*Family.*—Geraniaceae.

*Botanical.*—*Pelargonium zonale.*

*Common.*—*Pelargonium.*

*Designation.*—'KLEPZ16424'.

Parentage:

*Female parent.*—The female *pelargonium* variety 'KLEPZ05129' (U.S. Plant Pat. No. 18,621).

*Male parent.*—The proprietary male *pelargonium* variety SUNRISE Racing (unpatented).

Plant:

*Form.*—Bushy and round.

*Habit.*—Upright.

*Height.*—16.0 cm.

*Spread.*—25.0 cm.

*Natural flowering season.*—Spring to autumn.

*Propagation type.*—Vegetative cuttings.

*Time to produce a finished flowering plant.*—4 months.

*Time to initiate and develop roots.*—20 days.

*Root description.*—White and fine.

Stems:

*Quantity of stems per plant.*—4 to 5.

*Color.*—RHS 138A.

*Surface texture.*—Sparsely pubescent.

*Stem form.*—Round.

*Diameter.*—1.0 cm.

*Length.*—8.0 cm.

*Internode length.*—1.5 cm to 2.0 cm.

*Anthocyanin.*—Absent.

Leaves:

*Arrangement.*—Alternate.

*Shape.*—Transverse.

*Apex.*—Round.

*Base.*—Open.

*Margin.*—Crenate.

*Surface texture.*—Upper surface: Sparsely pubescent. Lower surface: Sparsely pubescent.

*Length.*—4.0 cm to 6.0 cm.

*Width.*—6.0 cm to 8.0 cm.

*Color.*—Upper surface: RHS N137B. Lower surface: RHS 137B.

*Petiole.*—Length: 4.0 cm to 6.0 cm. Diameter: 0.3 cm. Color: RHS 138A. Strength: Medium.

*Venation pattern.*—Palmate.

*Venation color.*—Upper surface: RHS 137B. Lower surface: RHS 138A.

Inflorescence:

*Lastingness of flowers on the plant.*—6 to 8 days.

*Umbels.*—Quantity of umbels per plant: 3 to 4. Length: 8.0 cm. Diameter: 11.0 cm.

*Individual florets of the umbel.*—Quantity of florets per umbel: Greater than 25. Depth: 2.0 cm. Diameter: 4.5 cm.

*Fragrance.*—Absent.

Flower buds:

*Cluster shape.*—Round.

*Cluster size.*—Length: 2.5 cm. Width: 3.0 cm.

*Surface texture.*—Moderately pubescent.

*Bud.*—Height: 0.8 cm. Width: 0.6 cm. Shape: Elliptic. Apex: Acute. Base: Obtuse. Margin: Entire. Color: RHS 138B.

Petals:

*Quantity per flower.*—5.

*Shape.*—Spatulate.

*Apex.*—Round.

*Base.*—Obtuse.

*Margin.*—Entire.

*Length.*—3.0 cm.

*Width.*—2.5 cm.

*Surface texture.*—Upper surface: Smooth. Lower surface: Smooth.

*Color of lobes.*—Upper lobes: Upper surface: RHS 43C with eye of RHS N57A. Lower surface: RHS 43D. Lower lobes: Upper surface: RHS 43C with eye of RHS N57A. Lower surface: RHS 43D.

Petaloids:

*Quantity per flower.*—0 to 2.

*Shape.*—Moderate.

*Apex.*—Acute.

*Base.*—Obtuse.

*Margin.*—Entire.

*Length.*—1.0 cm.

*Width.*—0.2 cm to 0.8 cm.

*Texture* (*both surfaces*).—Smooth.

*Color.*—Upper surface: RHS 43D. Lower surface: RHS 39D.

Sepals:

*Number per flower.*—5.

*Shape.*—Elliptic.

*Apex.*—Acute.

*Base.*—Obtuse.

*Margin.*—Entire.

*Surface texture.*—Upper surface: Smooth. Lower surface: Moderately pubescent.

*Color.*—Upper surface: RHS 138B. Lower surface: RHS 138B.

*Length.*—1.5 cm.

*Width.*—0.4 cm.

Pedicel:

*Length.*—2.0 cm.

*Diameter.*—0.15 cm.

*Color.*—RHS 138B.

*Surface texture.*—Sparsely pubescent.

*Strength.*—Medium.

Peduncle:

*Length.*—12.0 cm.

*Diameter.*—0.7 cm.

*Color.*—RHS 137B.

*Surface texture.*—Moderately pubescent.

*Strength.*—Medium to strong.

Reproductive Organs:

*Stamens.*—Quantity of stamens per flower: 5. Anther length: 0.2 cm. Filament length: 0.8 cm. Filament color: RHS 69D. Pollen amount: Moderate. Pollen color: RHS 31B.

*Pistils.*—Number: 1. Stigma color: RHS 38C. Style length: 0.3 cm. Style color: RHS 69D. Ovary arrangement: Central. Ovary color: RHS 138C. Ovary diameter: 0.3 cm. Ovary length: 0.1 cm.

Fruit and seed set: None observed.

Disease and pest/insect resistance: None observed.

COMPARISON WITH PARENTAL LINES AND KNOWN VARIETY

'KLEPZ16424' is distinguished from its parents as described in Table 1:

TABLE 1

Comparison with Parental Lines

| Characteristic | 'KLEPZ16424' | Female parent 'KLEPZ05129' | Male Parent SUNRISE Racing |
|---|---|---|---|
| Growth | Medium | Compact to Medium | Strong |
| Flower color | Salmon orange with purple eye | Orange | Salmon cerise |

TABLE 1-continued

Comparison with Parental Lines

| Characteristic | 'KLEPZ16424' | Female parent 'KLEPZ05129' | Male Parent SUNRISE Racing |
|---|---|---|---|
| Leaf zonation | Absent to very weak | Weak | Absent |

'KLEPZ16424' can be compared to the commercial variety 'Orangepen' (patent status unknown). Differences between the two varieties are described in Table 2:

TABLE 2

Comparison with Similar Variety

| Characteristic | 'KLEPZ16424' | Commercial line 'Orangepen' |
|---|---|---|
| Flower color | Salmon orange with purple eye | Orange |
| Flower size | Large | Medium |

We claim:

1. A new and distinct variety of *pelargonium* plant named 'KLEPZ16424' as illustrated and described herein.

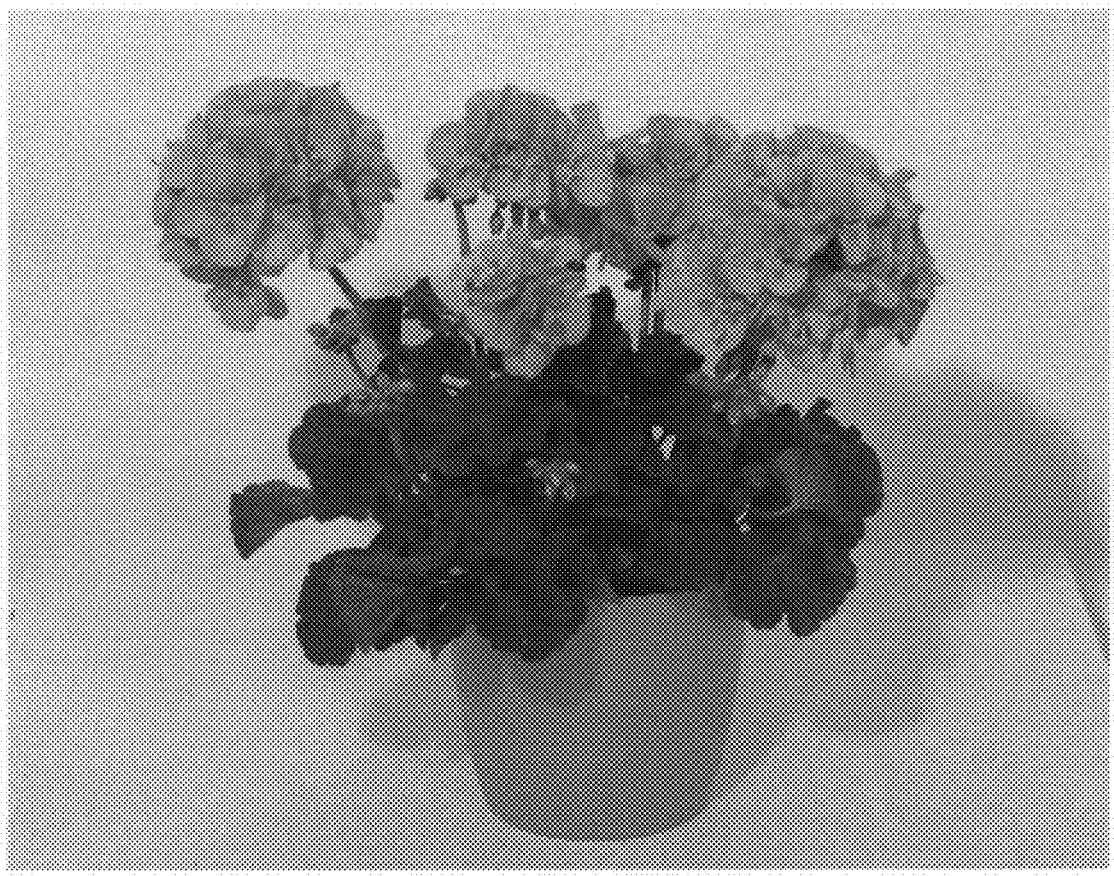

* * * * *